(12) United States Patent
Lai

(10) Patent No.: US 6,259,761 B1
(45) Date of Patent: Jul. 10, 2001

(54) METHOD OF AND APPARATUS FOR COLLECTING MORE VIEWS OF DATA IN A CT SCANNER WITH LIMITED DATA TRANSFER RATE

(75) Inventor: Ching-Ming Lai, Wakefield, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 09/377,334

(22) Filed: Aug. 18, 1999

(51) Int. Cl.⁷ .......................................................... A61B 6/03
(52) U.S. Cl. .............................................. 378/15; 378/901
(58) Field of Search .................... 378/4, 15, 19, 378/901

(56) References Cited

U.S. PATENT DOCUMENTS 4,691,233 * 9/1987 Acampora ....................... 375/240.05
4,794,455 * 12/1988 Ericsson .......................... 375/240.14
5,577,026   11/1996 Gordon et al. ........................ 370/24

\* cited by examiner

*Primary Examiner*—David V. Bruce
(74) *Attorney, Agent, or Firm*—McDermott, Will & Emery

(57) ABSTRACT

An apparatus for transferring an ordered sequence of data elements from a first location to a second location via a communication channel includes a multiplexor for selecting at least two primary data elements occurring at predetermined intervals within the series, and for selecting at least one intermediate data element occurring within the predetermined intervals between the primary data elements. The apparatus estimates, for each of the intermediate data elements, a value corresponding to the intermediate data element. Each of the estimated values is a predetermined function of an immediately preceding primary data element and an immediately subsequent primary data element in the ordered sequence. The apparatus calculates a difference value for each of the intermediate data elements. Each difference value is representative of a mathematical difference between the corresponding intermediate element and estimated value. The apparatus further includes a transmitter for transmitting each of the primary data elements and the difference elements along the communication channel.

28 Claims, 4 Drawing Sheets

METHOD OF AND APPARATUS FOR COLLECTING MORE VIEWS OF DATA IN A CT SCANNER WITH LIMITED DATA TRANSFER RATE

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

FIELD OF THE INVENTION

The present invention relates to methods of efficiently transferring digital data over a band-limited channel, and more particularly, to efficiently transferring data from a CT detector array to an image reconstruction computer via an existing data channel.

BACKGROUND OF THE INVENTION

It is well known to use electromechanical slip rings, to enable the transfer of data to and from a rotating device, such as the drum that is rotatably mounted in the gantry of a computer tomography (CT) scanner so that the X-ray equipment supported by the drum can be rotated about a patient during a tomographic scan. It is equally well known to employ a radio frequency (RF) link to enable such a data transfer. For example, U.S. Pat. No. 5,577,026, entitled "Apparatus for Transferring Data to and from a Moving Device," illustrates the use of an RF link to transfer data in a CT scanner.

U.S. Pat. Nos. 4,928,283 and RE 34,379 briefly describe a CT scan system employing a "two-way communication link" between "an electronics package" secured to the rotating disk of the system and a "computer used for image processing and control". No further detail is provided.

In a CT scanning system, the two-way communication link (hereinafter data link) typically has a maximum throughput rate that is not easily increased due to physical limitations of the components used to implement the data link. Thus, the number of views of raw data per rotation of the CT scanner is limited by the data transfer rate over the data link. However, the quality of the reconstructed image can be improved by using more views of data. For example, an existing CT system can collect and transfer up to 960 views per rotation. It has been shown that using 1440 to 1920 views per rotation significantly improves the reconstructed image, for example by reducing blurriness around the edges of the image. Increasing the number of views to be processed in existing systems is often difficult or impossible due to limitations of the data link throughput. One method of increasing the effective throughput rate of the data link without modifying the existing hardware components and configurations used to implement the data link is to utilize data compression techniques prior to transferring the raw data. However, conventional data compression techniques are generally not suitable for compressing raw CT data. First, the compression rate of a conventional compression algorithm is generally dependent upon the redundancy of the bit pattern in the data being compressed, i.e., the more repetition of the constituent bit patterns, the more the data will compress without the subsequent loss of data. Raw CT data tends to be highly random in the bit pattern, so the compression rate necessarily has to be low in order to preserve the data. As a result the available compression rate using conventional compression techniques are typically inadequate for CT applications. Second, the compression rates provided by conventional compression techniques are data dependent, and thus variable, which makes the transfer protocol more complex and the error checking more difficult in a CT application. Third, rare but relatively large loss in the compressed data can possibly cause destructive damage to the reconstructed CT image. Many conventional compression techniques were designed for applications that do not require that a constant data compression rate be maintained, or for applications that can tolerate an occasional large loss of data.

It is an object of the present invention to substantially overcome the above-identified disadvantages and drawbacks of the prior art, and to provide a data compression technique suitable for raw CT data.

SUMMARY OF THE INVENTION

The foregoing and other objects are achieved by the invention which in one aspect comprises an apparatus for transferring an ordered sequence of data elements from a first location to a second location via a communication channel. The apparatus includes a multiplexor for selecting at least two primary data elements occurring at predetermined intervals within the series, and for selecting at least one intermediate data element occurring within the predetermined intervals between the primary data elements. The apparatus further includes an estimator for determining, for each of the intermediate data elements, an estimated value corresponding to the intermediate data element. Each of the estimated values is a predetermined function of an immediately preceding primary data element and an immediately subsequent primary data element in the ordered sequence. The apparatus also includes a processor for calculating a difference value for each of the intermediate data elements. The difference value is a representative of a mathematical difference between the intermediate element and the corresponding estimated value. The apparatus further includes a transmitter for transmitting each of the primary data elements and the difference elements along the communication channel.

In another embodiment of the invention, the communication channel is band-limited, so as to define a maximum data throughput capability of the channel.

In another embodiment of the invention, the sequence of data elements is ordered corresponding to a plurality of angular positions of a rotatable device, relative to an associated stationary support structure, such that the predetermined intervals include an integral number of angular position increments.

In another embodiment of the invention, the predetermined interval is two angular position increments, such that one intermediate data element occurs between two consecutive primary data elements.

In another embodiment of the invention, the predetermined interval is four angular position increments, such that three intermediate data elements occur between two consecutive primary data elements.

In another embodiment of the invention, the sequence of data elements is ordered corresponding to a plurality of detectors from a detector array, corresponding to at least one angular position of a rotatable device. In this embodiment, the predetermined intervals include an integral number of detectors.

In another embodiment of the invention, the predetermined function includes a linear interpolation of two consecutive primary elements. When the interval between the two primary elements is two, the linear interpolation includes a mathematical average of two consecutive primary elements. When the interval between the two primary elements is three or more, the linear interpolation includes a weighted averaging, with linearly varying weights, of the two consecutive primary elements.

In another embodiment of the invention, the mathematical difference includes a limiting function, such that the difference value is limited to a maximum value when the calculated difference value exceeds the maximum value, and the difference value is limited to a minimum value when the calculated difference value exceeds the minimum value.

In another embodiment of the invention, the apparatus is used by a CT scanning system having a drum being rotatably mounted in a gantry support structure to transfer an ordered sequence of data elements from the drum to the gantry support structure via a communication channel.

BRIEF DESCRIPTION OF DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENTS

Figure 1:
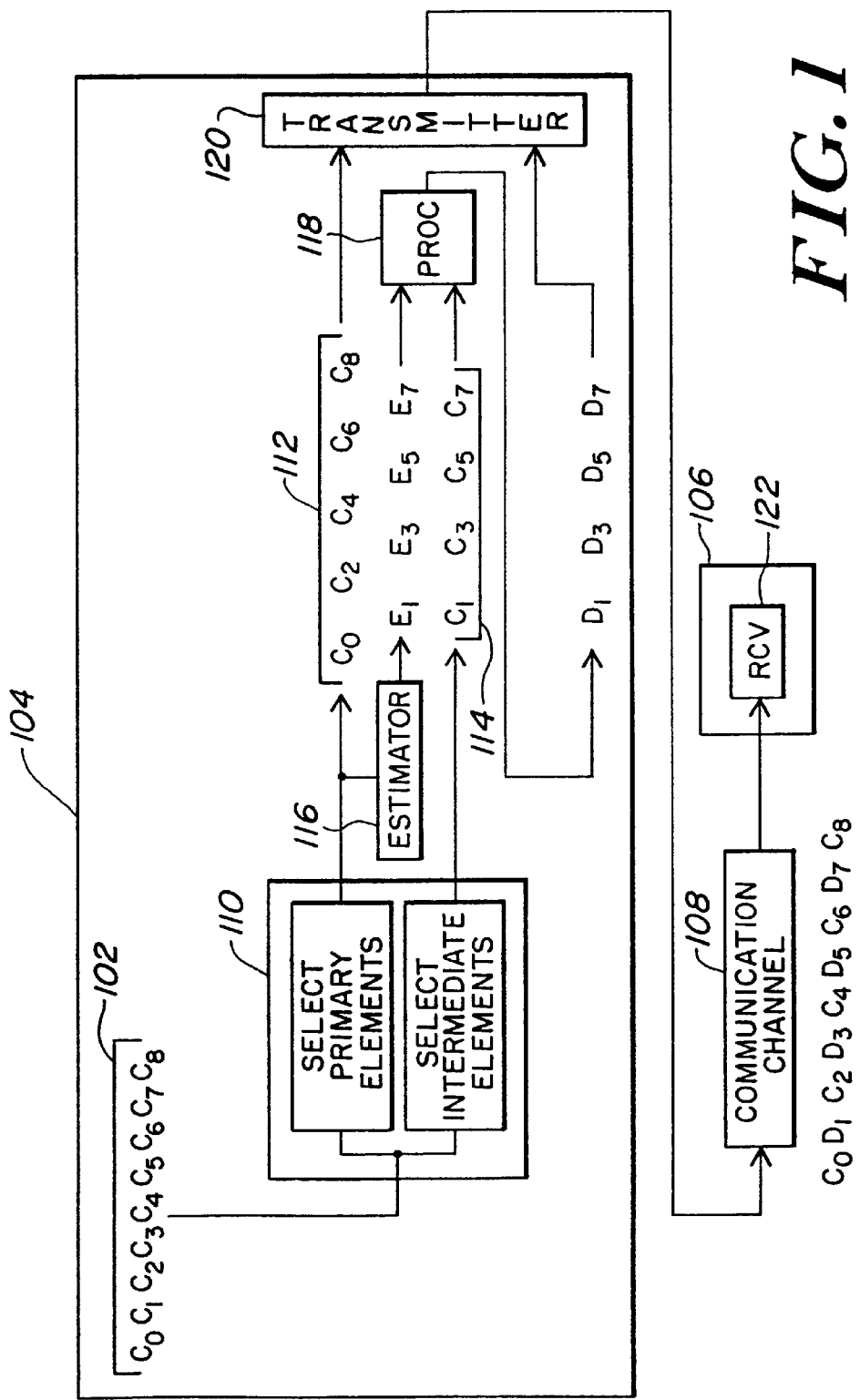
FIG. 1 shows a schematic view of one preferred embodiment of an apparatus for transferring an ordered sequence of data elements from a first location to a second location via a communication channel.

FIG. 1 shows a schematic view of one preferred embodiment of an apparatus 100 for transferring an ordered sequence of collected data elements 102 from a first location 104 to a second location 106 via a communication channel 108. The illustrated embodiment shows an exemplary sequence of nine collected data elements, $C_0$ through $C_8$. The apparatus 100 includes a multiplexor 110 for receiving the ordered sequence of data elements 102, and selecting primary data elements 112 and intermediate data elements 114 from the sequence 102. The primary data elements 112 occur at predetermined intervals within the series, and the intermediate data elements 114 occur within the predetermined intervals between the primary data elements 112.

Figure 2A:
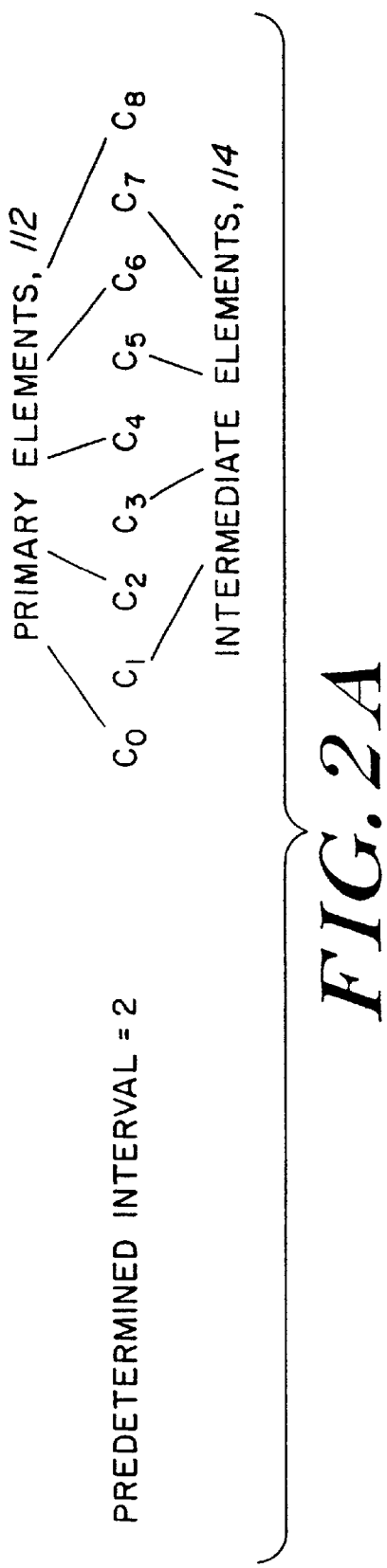
FIG. 2A illustrates the primary elements and the intermediate elements for the ordered sequence for a predetermined interval of two.
Figure 2B:
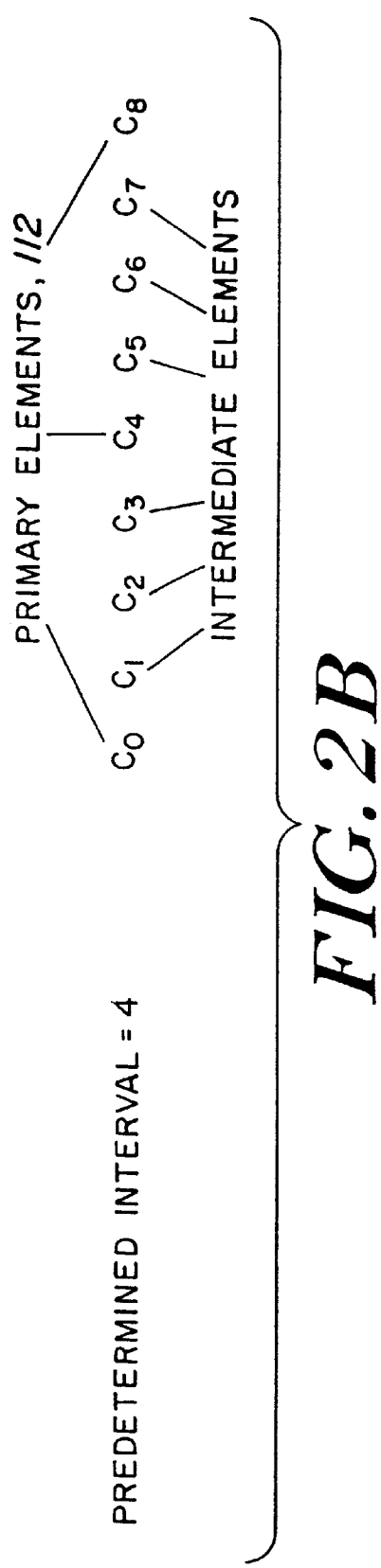
FIG. 2B illustrates the primary elements and the intermediate elements for the ordered sequence for a predetermined interval of four.

In the embodiment illustrated in FIG. 1, the predetermined interval is two, such that the primary elements 112 include $C_0$, $C_2$, $C_4$, $C_6$ and $C_8$, and the intermediate elements 114 include $C_1$, $C_3$, $C_5$, and $C_7$. In an alternative embodiment, the predetermined interval may include other values. For example, in one embodiment the predetermined interval may be four, such that the primary elements 112 include $C_0$, $C_4$ and $C_8$, and the intermediate elements 114 include $C_1$, $C_2$, $C_3$, $C_5$, $C_6$, and $C_7$. FIGS. 2A and 2B illustrate the primary elements 112 and the intermediate elements for the ordered sequence 102 for a predetermined interval of two and a predetermined interval of four, respectively. Although the exemplary embodiments explicitly show intervals between the 24 primary elements of two and four, other embodiments with intervals of 3, 5, 6, and other small intervals provide comparable results.

The apparatus further includes an estimator 116 for producing an estimated value $E_j$ for each of the intermediate elements 114, where j corresponds to the indexing subscript of each of the intermediate elements 114. In the embodiment shown in FIG. 1, the estimated values are $E_1$, $E_3$, $E_5$ and $E_7$, corresponding to $C_1$, $C_3$, $C_5$, and $C_7$, respectively. Each of the estimated values is an interpolation from the two nearest primary elements 112. In a preferred embodiment, the estimator 116 interpolates by averaging the two nearest primary elements to produce the estimate $E_j$. Thus, in the embodiment illustrated in FIG. 1 for a predetermined interval of two, the estimated value $E_1$ is the mathematical average of primary elements $C_0$ and $C_2$, the estimated value $E_3$ is the average of primary elements $C_2$ and $C_4$, the estimated value $E_5$ is the average of the primary elements $C_4$ and $C_6$, and the estimated value $E_7$ is the average of the primary elements $C_6$ and $C_8$. In other forms of the invention, the estimator 116 may interpolate using other known interpolation algorithms, including non-linear interpolation algorithms. In that case, more than two primary elements may be needed to perform such higher order interpolations. In general, a preferred embodiment of the estimator performs a linear interpolation of the two primary elements to produce an estimated value. As stated herein, at an interval of two, the interpolation is a mathematical average of the two primary elements with equal weight. At other interval values (e.g., at an interval of four as described herein), the interpolation is a weighted averaging of the two primary elements with linearly varying weights.

The apparatus 100 further includes a processor 118 for calculating a difference value $D_j$ corresponding to each of the intermediate elements 114. Each difference value $D_j$ represents the mathematical difference between a intermediate element 114 and the corresponding estimated value $E_j$, where j corresponds to the indexing subscript of each of the intermediate elements 114. Thus, in the illustrated embodiment, the difference values may be calculated as follows:

$$D_1 = C_1 - E_1, D_3 = C_3 - E_3, D_5 = C_5 - E_5, \text{ and } D_7 = C_7 - E_7.$$

The apparatus 100 further includes a transmitter 120 for receiving the primary data elements $C_0$, $C_2$, $C_4$, $C_6$ and $C_6$, and the difference values $D_1$, $D_3$, $D_5$, and $D_7$, combining the primary data elements and difference values according to a predetermined protocol, and transmitting the primary data elements and difference values via the communications channel 108.

At the second location 106, a receiver 122 receives the primary data elements and difference values from the communications channel 108. Since the difference values $D_j$ were generated by subtracting the corresponding estimated value from the corresponding intermediate data element, the receiver 122 can reconstruct the intermediate data elements from the primary data elements and difference values as follows:

$C_1=D_1+E_1$, $C_2=D_2+E_2$, $C_3=D_3+E_3$, and $C_4=D_4+E_4$.

Figure 3:
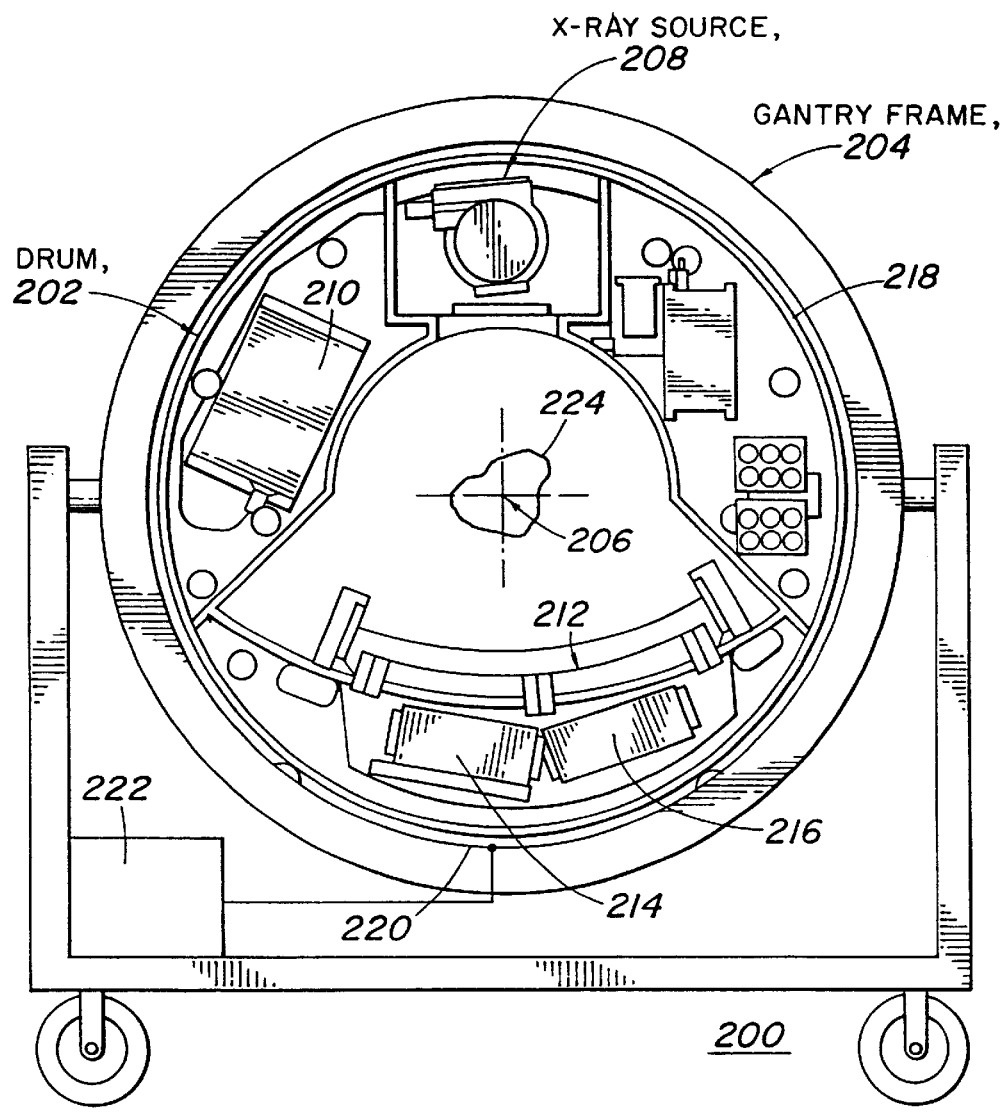
FIG. 3 illustrates an end view of a typical CT scanner.

The present invention is especially useful when used in conjunction with a system that produces an ordered sequence of collected data elements 102, the values of which do not change appreciably from one element to the next. As an example, consider a typical CT scanning system 200 as shown in FIG. 3. This scanning system 200 includes a drum assembly 202 rotatably mounted to a stationary gantry frame 204 such that the drum assembly 202 rotates about a rotation axis 206. An X-ray source 208 and its associate drive circuitry 210, a detector array 212, a data acquisition system 214 (hereinafter DAS), a rotating RF receiver/transmitter assembly 216 and a rotating antenna assembly 218 are mounted to the rotatable drum assembly 202. A stationary antenna assembly 220 and a stationary receiver/transmitter 222 are mounted to the gantry frame 204. The X-ray source 208 directs X-ray radiation toward the detector array 212, such that the X-ray radiation passes through an object 224 located at the rotation axis 206. The drum assembly 202 rotates with respect to the object 224, so the X-ray radiation passes through the object 224 at different angles (referred to as view angles, or equivalently, views) as the drum assembly 202 rotates. The object 224 is typically not uniform, so the attenuation characteristic through the object varies as the view angle varies. At each of a plurality of substantially uniform angular increments of the drum assembly (each angular increment corresponding to a view), the DAS 214 samples the detector array 212 and conveys the sampled data to the receiver/transmitter assembly 216. The receiver/transmitter assembly 216 modulates the sampled data onto a carrier signal and applies the modulated carrier signal to the rotating antenna assembly 218. The stationary receiver/transmitter 222 receives and demodulates the modulated carrier so as to extract the sampled data, and provides the sampled data to a reconstruction computer (not shown). An example of such a system for conveying data from the drum to the gantry of a CT scanning system is provided in U.S. Pat. No. 5,577,026, entitled "Apparatus for Transferring Data to and From a Moving Device," and is hereby incorporated by reference.

In a representative CT scanning system, the angular increment between views is approximately 0.375 degrees, so as to define 960 views through the object 224 for each complete rotation of the drum assembly 202. Because the angular increment between views is relatively small, the attenuation characteristics for adjacent views (corresponding to adjacent angular positions of the drum 202) tend to be similar. The data sampled from the detector array 212 is a direct function of the attenuation characteristic of the corresponding view, so the data sets taken from the detector array 212 for adjacent views tend to be similar (on a detector by detector basis). Thus, the data at a given detector in the detector array 212 changes relatively slowly from view to view as the drum 202 rotates. The apparatus illustrated in FIG. 1 may be used to efficiently transfer data taken from an individual detector in the detector array 212 as the drum 202 rotates.

In general, there may be N individual detectors in the detector array 212 such that each detector defines a data channel. Further, there may be M total views in a complete rotation of the drum assembly 202, with the view number ranging from 0 to M−1. Let $C_i(k)$ be the collected data value from $i^{th}$ detector at the $2k^{th}$ view, then the primary views may be given by:

$C_i(2k)$ with $k=0,1, \ldots, (M-2)/2$ and $i=1,2, \ldots, N$ and the intermediate views are given by:

$C_i(2k+1)$ with $k=0,1, \ldots, (M-2)/2$ and $i=1,2, \ldots, N$

In a preferred embodiment, each primary and intermediate view is represented by a 16-bit word with 2-bit exponent and 14-bit mantissa. Let $C_i'(2k)$ be the mantissa part of $C_i(2k)$. Using linear interpolation, the difference value $D_i(2k+1)$ corresponding to the intermediate view $C_i(2k+1)$ is given by:

$$D_i(2k+1)=C_i'(2k+1)-(C_i'(2k)+C_i'(2k+2))/2 \qquad (1)$$

with $k=0,1, \ldots, (M-2)/2$ and $i=1,2, \ldots, N$. The values $C_i'(2k+1)$ and $C_i'(2k+2)$ are the mantissa parts of $C_i(2k+1)$ and $C_i(2k+2)$, respectively, after they are converted to have an exponent common to $C_i(2k)$. The value $D_i(2k+1)$ is the mantissa part of the difference value having the same 2-bit exponent as $C_i(2k)$. In one embodiment, the value $D_i(2k+1)$ may be further encoded as follows to guarantee a consistent 8 bit data unit:

$E_i(2k+1)=D_i(2k+1)$ if $-128 \leq D_i(2k+1) \leq 127$ and $E_i(2k+1)=-128$ if $D_i(2k+1)<-128$ $$E_i(2k+1)=127 \text{ if } D_i(2k+1)>127 \qquad (2)$$

$E_i(2k+1)$ is thus limited to the upper and lower bound of a signed 8-bit data unit. The 8-bit value $E_i(2k+1)$ is then packed with the $E_i(2k+3)$ into one word as the compressed data of odd view numbers $2k+1$ and $2k+3$.

To further increase the dynamic range of the encoded difference value $E_i(2k+1)$, a 2-bit common exponent, also called block exponent, common to $D_i(2k+1)$ and $D_i(2k+3)$ is calculated. This 2-bit block exponent $B_i(2k+1)$ of channel i can be packed into a 16 bit data unit with the block exponents of the adjacent 7 channels into one word for decoding. If $D_i'(2k+1)$ is the mantissa part with this $D_i(2k+1)$ under this block exponent, it will be encoded into 8 bits as described hereinbefore, i.e., $E_i(2k+1)=D_i'(2k+1)$ if $-128 \leq D_i'(2k+1) \leq 127$ and $E_i(2k+1)=-128$ if $D_i'(2k+1)<-128$ $$E_i(2k+1)=127 \text{ if } D_i'(2k+1)>127 \qquad (3)$$

After the data are transferred, the data of odd number views are decoded from the compressed data. A recovered difference value $F_i(2k+1)$ is decoded from the mantissa value $E_i(2k+1)$ and the block exponent $B_i(2k+1)$ as:

$$F_i(2k+1)=E_i(2k+1)*2^{Bi(2k+1)}. \qquad (4)$$

Also, a recovered difference value $F_i(2k+3)$ is decoded as:

$$F_i(2k+3)=E_i(2k+3)*2^{Bi(2k+1)}. \qquad (5)$$

Substituting the decoded value $F_i(2k+1)$ for the difference value $D_i(2k+1)$ in Equation (1), the mantissa part of the intermediate view $C_i(2k+1)$ can be calculated as:

$$C_i'(2k+1)=F_i(2k+1)+(C_i'(2k)+C_i'(2k+2))/2 \qquad (6)$$

The recovered, "decompressed" intermediate value $C_i(2k+1)$ consists of the mantissa value $C_i'(2k+1)$ given in Equation (6) and the 2-bit exponent inherited from $C_i(2k)$.

The data compression rate for the views conveyed via the encoded data is approximately 2 to 1. Therefore, the CT system can collect 1920 total views, compress 960 of the 1920 views to the equivalent data block size of 480 views of uncompressed data, while keeping the other 960 views unaffected. Suppose an existing CT system includes a communication link between the rotating components and the stationary components that has a maximum data throughput capability of 1440 views per rotation of the drum assembly. Such a CT system using the illustrated embodiment of the apparatus could collect 1920 views of data but transfer them as if they were 960+480=1440 views of data. Similarly, for a system having a communications link with a maximum throughput of 960 views per rotation, the system using this embodiment of the invention could collect 1280 views and transfer the data as if they were 640+320=960 views of data.

Figure 4:
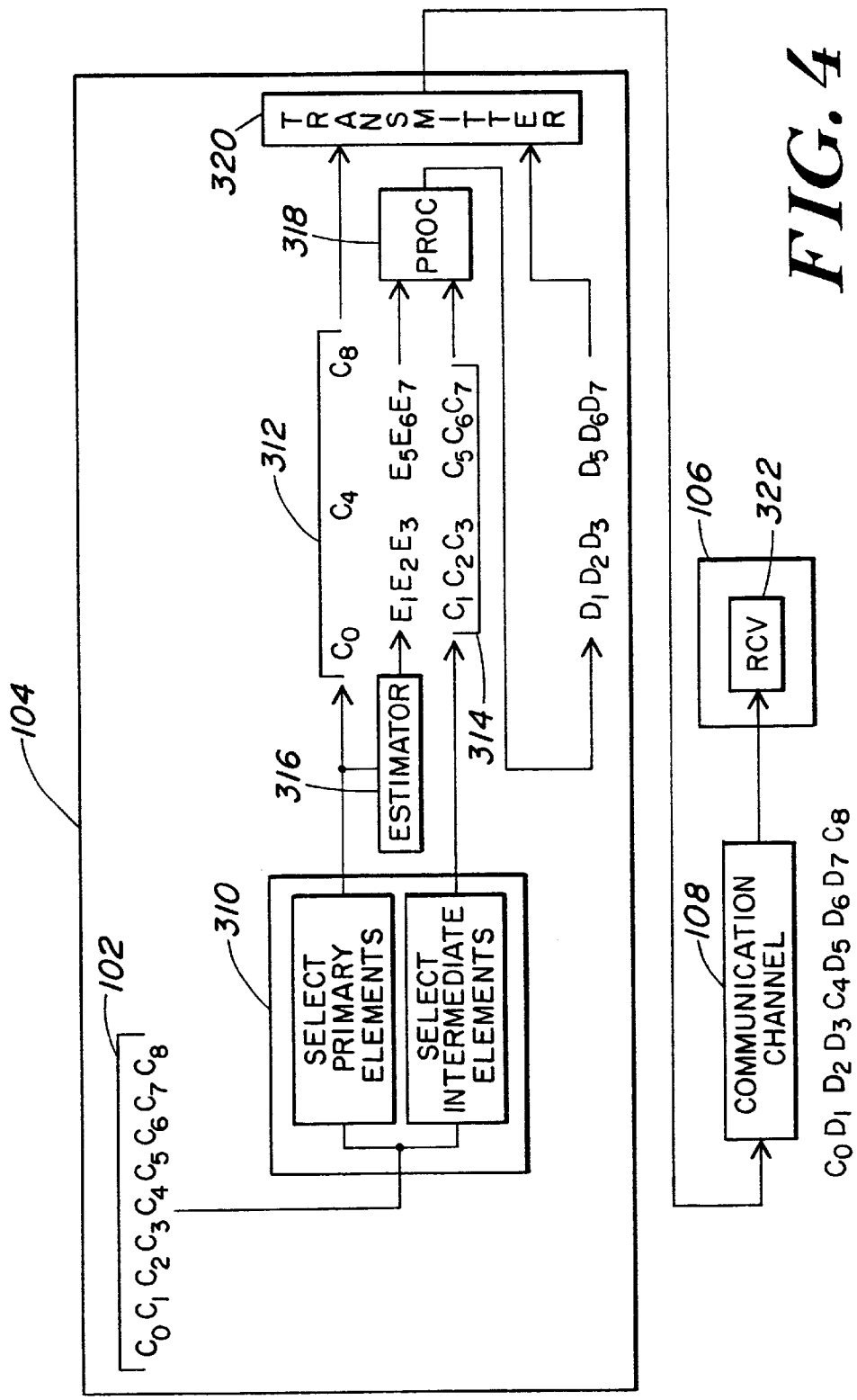
FIG. 4 illustrates another embodiment of the apparatus shown in FIG. 1.

Another embodiment of the apparatus 100 according to the present invention is shown schematically in FIG. 4. This embodiment estimates (and thereby compresses) the data from 3 out of every 4 views. The data in one of every 4 views remain intact. A multiplexor 310 separates the collected data elements 102 into primary data elements 312 and intermediate data elements 314. The primary data elements 312, given by:

$$C_i(4k) \text{ with } k=0,1,\ldots,(M-4)/4 \text{ and } i=1,2,\ldots,N$$

are transferred without alteration, in the original 16-bit word format.

Similar to the embodiment shown in FIG. 1, an estimator 316 produces an estimated value for each of the intermediate elements 314, and the difference values for the embodiment shown in FIG. 4 are calculated by processor 318 as:

$$D_i(4k+1)=C_i'(4k+1)-(3C_i'(4k)+C_i'(4k+4))/4$$

$$D_i(4k+2)=C_i'(4k+2)-(C_i'(4k)+C_i'(4k+4))/2$$

$$D_i(4k+3)=C_i'(4k+3)-(C_i'(4k)+3C_i'(4k+4))/4 \quad (7)$$

with $k=0,1,\ldots,(M-4)/4$ and $i=1,2,\ldots,N$. The values $C_i'(4k+1)$, $C_i'(4k+2)$, $C_i'(4k+3)$, and $C_i'(4k+4)$ are the mantissa parts of $C_i(4k+1)$, $C_i(4k+2)$, $C_i(4k+3)$, and $C_i(4k+4)$, respectively, after they are converted to share an exponent common to $C_i(4k)$. The values $D_i(4k+1)$, $D_i(4k+2)$ and $D_i(4k+3)$ represent the mantissa part of the corresponding difference value under the 2-bit exponent of $C_i(4k)$.

A 2-bit block exponent may be calculated from $D_i(4k+1)$, $D_i(4k+2)$, and $D_i(4k+3)$ as described herein for the embodiment shown in FIG. 1. This 2-bit block exponent $B_i(4k+1)$ of channel i is packed with that of adjacent 8 detector channels into one word for subsequent decoding. It should be noted that $B_i(4k)$, $B_i(4k+2)$, and $B_i(4k+3)$ do not exist; only one block exponent is defined for every 4 views of each detector channel.

The value $D_i'(4k+1)$, i.e., the mantissa part corresponding to $D_i(4k+1)$ under this block exponent, is encoded into the 8 bit value $E_i(4k+1)$ as:

$$E_i(4k+1)=D_i'(4k+1) \text{ if } -128 \leq D_i'(4k+1) \leq 127$$

and $$E_i(4k+1)=-128 \text{ if } D_i'(4k+1)<-128$$

$$E_i(4k+1)=127 \text{ if } D_i'(4k+1)>127 \quad (8)$$

The mantissa parts $D_i'(4k+2)$ and $D_i'(4k+3)$ (corresponding to $D_i(4k+2)$ and $D_i(4k+3)$, respectively) are similarly encoded into $E_i(4k+2)$ and $E_i(4k+3)$, respectively.

After the data are transferred by processor 320 via the communication channel 108 to the receiver 322, the data of the compressed views are decoded by the receiver 322 from the encoded data. Based on the mantissa value $E_i(4k+1)$ and the block exponent $B_i(4k+1)$, the difference value is decoded as:

$$F_i(4k+1)=E_i(4k+1)*2^{Bi(4k+1)}$$

and $$F_i(4k+2)=E_i(4k+2)*2^{Bi(4k+1)}$$

$$F_i(4k+3)=E_i(4k+3)*2^{Bi(4k+1)} \quad (9)$$

Using the decoded value $F_i(4k+1)$ for the difference value $D_i(4k+1)$ in Equation (7), the mantissa parts of $C_i(4k+1)$, $C_i(4k+2)$ and $C_i(4k+3)$ are calculated as:

$$C_i'(4k+1)=F_i(4k+1)+(3C_i'(4k)+C_i'(4k+4))/4$$

and $$C_i'(4k+2)=F_i(4k+2)+(C_i'(4k)+C_i'(4k+4))/2$$

$$C_i'(4k+3)=F_i(4k+3)+(C_i'(4k)+3C_i'(4k+4))/4 \quad (10)$$

The decompressed value $C_i(4k+1)$ includes the mantissa value $C_i'(4k+1)$ given in Equation (10) and the 2-bit exponent inherited from $C_i(4k)$.

As with the embodiment illustrated in FIG. 1, the data compression rate for the views conveyed via the encoded data is approximately 2 to 1 in this embodiment. Therefore, the CT system c an collect 1920 total views, compress 1440 of the 1920 views to the equivalent data block size occupied by 720 views of uncompressed data, while transferring the remaining 480 views unaffected (i.e., without compression). The existing CT system described hereinbefore (having a communication link with a maximum data throughput capability of 1440 views per rotation of the drum assembly) could conceivably collect 1920 views of data, but transfer them as if they were 480+720=1200 views of data. Thus, 1920 views may be transferred in the bandwidth equivalent of 1200 uncompressed views. This represents only a 25 percent increase as compared to the current practice of collecting and transferring 960 views of uncompressed data.

In other embodiments, the sequence of data elements may be provided by a single detector from an array over a number of views, rather than some or all of the detectors in an array for a given view, as is described by the exemplary embodiments herein, or by some combination thereof.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. An apparatus for transferring an ordered sequence of data elements from a first location to a second location via a communication channel, comprising:
   a multiplexor for selecting at least two primary data elements occurring at predetermined intervals within said series, and for selecting at least one intermediate data element occurring within said predetermined intervals between said primary data elements;

an estimator for determining, for each of said intermediate data elements, a plurality of estimated values corresponding to said intermediate data elements, each of said estimated values being a predetermined function of an immediately preceding primary data element and an immediately subsequent primary data element in said ordered sequence;

a processor for calculating a difference value for each of said intermediate data elements, said difference value being representative of a mathematical difference between said intermediate element and said corresponding estimated value; and a transmitter for transmitting each of said primary data elements and said difference elements along said communication channel.

2. An apparatus according to claim 1, further including a receiver for receiving said primary data elements and said difference elements from said communication channel and for recovering said intermediate elements from said primary data elements and said difference elements.

3. An apparatus according to claim 1, each of said ordered sequence of data elements including an exponent portion and a mantissa portion, wherein said estimated values and said difference values are generated by operating on said mantissa portion.

4. An apparatus according to claim 3, wherein said estimated values and said difference values include an exponent portion that is common to a corresponding primary data element.

5. An apparatus according to claim 3, wherein said difference values include a block exponent value that is common to adjacent difference values within said ordered sequence.

6. An apparatus according to claim 1, wherein said communication channel is substantially band-limited, so as to define a maximum data throughput capability of said channel.

7. An apparatus according to claim 1, wherein said sequence of data elements is ordered corresponding to a plurality of angular positions of a rotatable device, relative to an associated stationary support structure, such that said predetermined intervals include an integral number of angular position increments.

8. An apparatus according to claim 7, wherein said predetermined interval is two angular position increments, such that one intermediate data element occurs between two consecutive ones of said at least two primary data elements.

9. An apparatus according to claim 7, wherein said predetermined interval is four angular position increments, such that three intermediate data elements occur between two consecutive ones of said at least two primary data elements.

10. An apparatus according to claim 1, wherein said sequence of data elements is ordered corresponding to a plurality of detectors from a detector array corresponding to at least one angular position of a rotatable device, relative to an associated stationary support structure, such that said predetermined intervals include an integral number of detectors.

11. An apparatus according to claim 1, wherein said predetermined function includes a linear interpolation of two consecutive ones of said at least two primary data elements.

12. An apparatus according to claim 11, wherein said linear interpolation includes a mathematical average.

13. An apparatus according to claim 11, wherein said linear interpolation includes a weighted averaging of the two primary elements with a plurality of linearly varying weights.

14. An apparatus according to claim 1, wherein said mathematical difference includes a limiting function, such that said difference value is limited to a maximum value when said calculated difference value exceeds said maximum value, and said difference value is limited to a minimum value when said calculated difference value exceeds said minimum value.

15. In a CT scanning system having a drum being rotatably mounted in a gantry support structure, an apparatus for transferring an ordered sequence of data elements from said drum to said gantry support structure via a communication channel, comprising:

a multiplexor for selecting at least two primary data elements occurring at predetermined intervals within said series, and for selecting at least one intermediate data element occurring within said predetermined intervals between said primary data elements;

an estimator for determining, for each of said intermediate data elements, an estimated value corresponding to said intermediate data element, each of said estimated values being a predetermined function of an immediately preceding primary data element and an immediately subsequent primary data element in said ordered sequence;

a processor for calculating a difference value for each of said intermediate data elements, said difference value being representative of a mathematical difference between said intermediate element and said corresponding estimated value; and a transmitter for transmitting each of said primary data elements and said difference elements along said communication channel.

16. An apparatus according to claim 15, each of said ordered sequence of data elements including an exponent portion and a mantissa portion, wherein said estimated values and said difference values are generated by operating on said mantissa portion.

17. An apparatus according to claim 16, wherein said estimated values and said difference values include an exponent portion that is common to a corresponding primary data element.

18. An apparatus according to claim 16, wherein said difference values include a block exponent value that is common to adjacent difference values within said ordered sequence.

19. An apparatus according to claim 15, wherein said communication channel is substantially band-limited, so as to define a maximum data throughput capability of said channel.

20. An apparatus according to claim 15, wherein said sequence of data elements is ordered corresponding to a plurality of angular positions of a rotatable device, relative to an associated stationary support structure, such that said predetermined intervals include an integral number of angular position increments.

21. An apparatus according to claim 20, wherein said predetermined interval is two angular position increments, such that one intermediate data element occurs between two consecutive primary data elements.

22. An apparatus according to claim 20, wherein said predetermined interval is four angular position increments, such that three intermediate data elements occur between two consecutive primary data elements.

23. An apparatus according to claim 15, wherein said predetermined function includes a mathematical average.

24. An apparatus according to claim 15, wherein said mathematical difference includes a limiting function, such that said difference value is limited to a maximum value when said calculated difference value exceeds said maximum value, and said difference value is limited to a minimum value when said calculated difference value exceeds said minimum value.

25. A method of transferring an ordered sequence of data elements from a first location to a second location via a communication channel, comprising the steps of:

identifying at least two primary data elements occurring at predetermined intervals within said series, and identifying at least one intermediate data element occurring within said predetermined intervals between said primary data elements;

for each of said intermediate data elements, determining an estimated value corresponding to said secondary data element, each of said estimated values being a predetermined function of an immediately preceding primary data element and an immediately subsequent primary data element in said ordered sequence;

calculating a difference value for each of said intermediate data elements, said difference value being representative of a mathematical difference between said intermediate element and said corresponding estimated value; and transferring each of said primary data elements and said difference elements along said communication channel.

26. A method according to claim 25, wherein said step of determining said estimated value further includes the step of generating a mathematical average of an immediately preceding primary data element and an immediately subsequent primary data element in said ordered sequence.

27. A method according to claim 25, wherein said step of calculating said difference value further includes the step of limiting said difference values, such that said difference value is limited to a maximum value when said calculated difference value exceeds said maximum value, and said difference value is limited to a minimum value when said calculated difference value exceeds said minimum value.

28. An apparatus for transferring an ordered sequence of data elements, from a first location to a second location, as compressed data via a band limited communication channel, comprising:

at least one data generator arranged and constructed so as to generate the sequence of data elements, some of the data elements being designated primary data elements and some of the data elements being designated intermediate data elements;

at least one data estimator constructed and arranged so as to provide estimated data elements corresponding to the intermediate data elements, with each estimated data element being a function of at least two primary data elements;

at least one processor for calculating the difference between each estimated data element and the corresponding designated intermediate data element so as to generate a difference data element such that the difference data element is small in comparison to the value of the corresponding intermediate data element; and a transmitter constructed and arranged so as to transfer the primary data elements and the difference data elements from the first location.

* * * * *